(12) United States Patent
Pazouki

(10) Patent No.: US 9,402,785 B1
(45) Date of Patent: Aug. 2, 2016

(54) VIAL AND CAP HOLDER FOR A MEDICAL PROCEDURE

(71) Applicant: Narges Pazouki, Turlock, CA (US)

(72) Inventor: Narges Pazouki, Turlock, CA (US)

( * ) Notice: Subject to any disclaimer, the term of this patent is extended or adjusted under 35 U.S.C. 154(b) by 0 days.

(21) Appl. No.: 14/500,965

(22) Filed: Sep. 29, 2014

(51) Int. Cl.
 *A45F 5/00* (2006.01)
 *A61J 1/16* (2006.01)

(52) U.S. Cl.
 CPC .......................................... *A61J 1/16* (2013.01)

(58) Field of Classification Search
 CPC .... B25H 3/04; A47F 7/0028; A47G 25/0657; A47G 23/0241; A47G 29/08; A45F 5/10; F16L 3/13; F16L 3/2235; B60R 1/076; B65D 85/20; A61J 1/16
 See application file for complete search history.

(56) References Cited

U.S. PATENT DOCUMENTS

| | | | | |
|---|---|---|---|---|
| D263,062 S | * | 2/1982 | Rasmussen | D21/402 |
| 5,375,726 A | * | 12/1994 | Lechleiter | 211/74 |
| 5,615,782 A | * | 4/1997 | Choe | 211/70.6 |
| 7,506,770 B2 | * | 3/2009 | Rief | 211/70.6 |
| D597,403 S | * | 8/2009 | Ho et al. | D8/396 |
| 8,020,259 B2 | * | 9/2011 | Ho et al. | 24/129 R |

OTHER PUBLICATIONS

Funrise.com—"Gazillion 33-in-1 Incredibubble Wand", www.funrise.com/detail.aspx?id=38079 and www.youtube.com/watch?v=u_Jpe2O_vzg, Jun. 12, 2014.*

* cited by examiner

*Primary Examiner* — Stephen Vu
(74) *Attorney, Agent, or Firm* — Law Office of Rodney LeRoy

(57) ABSTRACT

A vial and cap holder includes a vial frame having a plurality of vial apertures formed therein, wherein each vial aperture is configured to receive a vial, and a handle connected to the vial frame. The vial and cap holder further includes a plurality of cap holders connected to the vial frame. Each of the cap holders is positioned adjacent to one of the apertures on the vial frame, and each cap holder is configured to hold a cap for capping a vial. Each of the cap holders is configured to hold a cap above a top of vials configured to be held by the vial apertures. Corresponding ones of the vial holders and the cap holders are positioned along common radiuses of the vial frame.

20 Claims, 7 Drawing Sheets

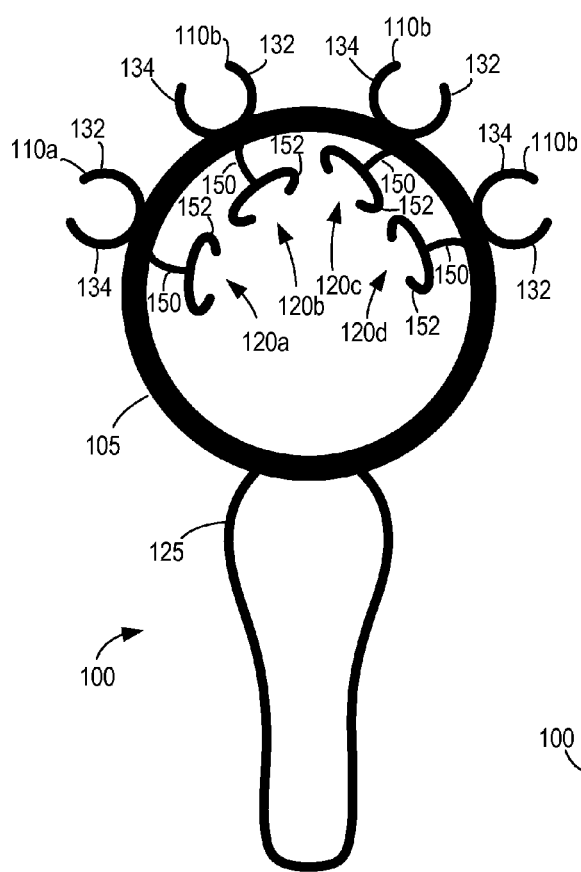
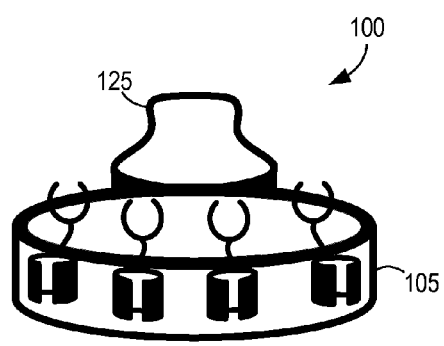
FIG. 1B
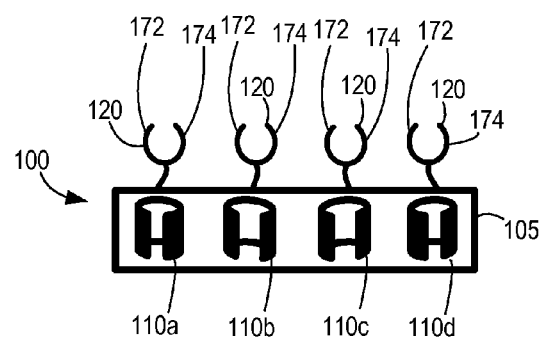
FIG. 1A
FIG. 1C

VIAL AND CAP HOLDER FOR A MEDICAL PROCEDURE

BACKGROUND OF THE INVENTION

The present invention generally relates to medical instruments used for medical procedures, and more specifically relates to a vial and cap holder used for a medical procedure.

Medical samples are often taken from a medical patient for diagnosis to determine the patient's health. After a medical sample is taken from a patient, the medical sample is often placed in a container that can be sealed for transport to a diagnostic facility. Containers that used for medical sample storage and transport are typically sterile and are designed to prevent samples from becoming contaminated. After a container with its sample is transported to a diagnostic facility, the sample is removed from the container and is tested according to one or more of a variety of assays.

A vial and a cap used together are one type of container that is often used by medical practitioners for storing and transporting medical samples. A capped vial provides a relatively sterile environment for sample storage and transport.

A medical practitioner using a vial and a cap for sample storage may take a medical sample from a patent, place the medical sample in the vial while the vial is held in one hand, and place the cap on the vial with the other hand. The steps of holding a vial, placing a medical sample inside the vial, and then capping the vial may appear relatively simple, but these steps are often performed while a medical practitioner is performing a medical procedure on a patient. While the medical practitioner is performing the medical procedure, the medical practitioner may also be operating one or more other pieces of medical equipment, interacting with other medical practitioners, and managing the patient. For example, during a lumbar puncture, amniocentesis, paracentesis, or other fluid collection procedure, a puncture needle needs to be managed, a syringe or tubing connected to the puncture needle might need to be managed, and a manometer might be used and need to be managed. Various and other medical devices might also need to be managed while fluid is collected in a vial and then capped. If numerous medical samples are being taken during the medical procedure, then multiple vials and caps might need to be managed while other medical equipment is also managed. These multiple devices and steps being performed substantially simultaneously end up with the simple procedure of placing a medical sample in a vial and capping the vial with a cap relatively complex.

Embodiments of the instant invention are directed at simplifying such medical procedures and thereby improving patient care.

BRIEF SUMMARY OF THE INVENTION

The present invention generally provides a medical instrument used for medical procedures, and more specifically provides a vial and cap holder used for a medical procedure, such as a lumbar puncture, amniocentesis, paracentesis, or other fluid collection procedure.

According to one embodiment, a vial and cap holder includes a vial frame, and a handle connected to the vial frame. The vial and cap holder further includes a plurality of vial holders connected to an outer surface of the vial frame. Each vial holder is configured to receive and hold a vial. The vial and cap holder further includes a plurality of cap holders connected to an inner surface of the vial frame. Each of the cap holders is positioned opposite to a corresponding one of the vial holders on the vial frame, and each cap holder is configured to hold a cap for capping a vial.

According to a specific embodiment, the vial frame is a loop. The loop can be a quadrilateral loop.

According to another specific embodiment, each of the vial holders includes a tube. The tubes can be cylinders. Further, the tubes can each have an opening formed in a side of the tube such that the tube is configured to flex away from the opening and towards the opening. In a position where each of the tubes is flexed away from the opening in the tube, the tube is configured to exert and inward force on a vial positioned in the tube. In one embodiment, each of the openings extends from a first end of a tube to a second end of the tube.

According to another specific embodiment, each of the cap holders includes an extension member, and a cap clasp. Each of the extension members connects to the vial frame and connects to one of the cap clasps. Each of the cap clasps can include a closed ring, or can include a first arm and a second arm that are configured to flex to hold a cap for a vial.

According to another specific embodiment, adjacent ones of the vial holders are positioned at thirty degrees or less apart along the vial frame with respect to a center of the vial frame. Corresponding ones of the vial holders and the cap holders are positioned along common radiuses of the vial frame.

According to one embodiment, a vial and cap holder includes a vial frame having a plurality of vial apertures formed therein. Each vial aperture is configured to receive a vial. The vial and cap holder further includes a handle connected to the vial frame, and a plurality of cap holders connected to the vial frame. Each of the cap holders is positioned adjacent to one of the apertures on the vial frame. Each cap holder is configured to hold a cap for capping a vial. Each of the cap holders is configured to hold a cap above a top of a vial that is held by one of the vial apertures. Corresponding ones of the vial holders and the cap holders are positioned along common radiuses of the vial frame.

According to a specific embodiment, each of the cap holders is configured to allow a cap held by the cap holder to rotate with respect to the cap holder for threading the cap onto a vial.

According to another specific embodiment, each of the cap holders includes an extension member, and a cap clasp. Each of the extension members connects to the vial frame and connects to one of the cap clasps.

According to another specific embodiment, the cap clasp includes a closed ring, or includes a first arm and a second arm that are configured to flex to hold a cap for a vial.

According to one embodiment, a vial and cap holder includes a vial frame, and a handle connected to the vial frame. The vial and cap holder further includes a plurality of vial holders connected to an outer surface of the vial frame. Each vial holder is configured to receive and hold a vial. The vial and cap holder further includes a plurality of cap holders connected to an inner surface of the vial frame. Each of the cap holders is positioned opposite to a corresponding one of the vial holders on the vial frame, and each cap holder is configured to hold a cap for capping a vial. Each of the vial holders and each of the cap holders include a cylindrical tube having an opening formed in a side of the cylindrical tube and the cylindrical tube is configured to flex away from the opening and towards the opening for holding a vial and cap, respectively. Each of the cap holders is configured to hold a cap above a top of a vial that is held by one of the vial apertures. Corresponding ones of the vial holders and the cap holders are positioned along common radiuses of the vial frame. According to a specific embodiment, adjacent ones of the vial holders are positioned at thirty degrees or less apart along the vial frame with respect to a center of the vial frame.

The embodiments described herein provide a number of benefits and advantages for medical personal and patients that will be readily apparent after review of the following detailed description, claims, and appended figures.

BRIEF DESCRIPTION OF THE DRAWINGS

FIG. 1A is a top view of a vial and cap holder according to one embodiment of the present invention.

FIGS. 1B and 1C are a perspective view and a front planar view of the vial and cap holder and show the vial holders attached to an outer surface of the clasp frame according to one embodiment.

DETAILED DESCRIPTION OF THE INVENTION

Figure 2A:
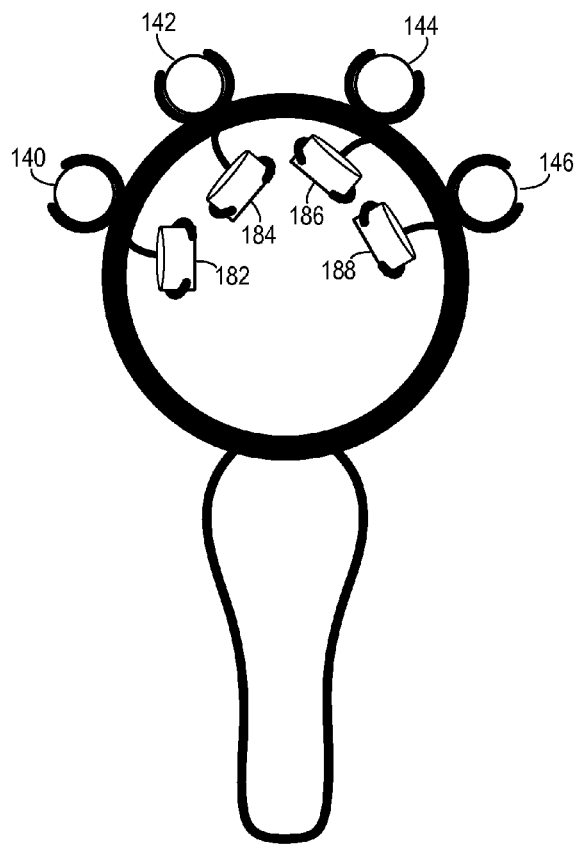
FIGS. 2A, 2B, and 2C are a top view, a perspective view, and a front view of the vial and cap holder holding a number of vials in the vial holders.

The present invention generally provides a medical instrument used for medical procedures, and more specifically provides a vial and cap holder used for a medical procedure, such as a lumbar puncture, amniocentesis, paracentesis, or other fluid collection procedures.

FIG. 1A is a top view of a vial and cap holder 100 according to one embodiment of the present invention. The vial and cap holder includes a clasp frame 105, vial holders 110a, 110b, 110c, and 110d (generally 110), cap holders 120a, 120b, 120c, and 120d (generally 120), and a handle 125. Various embodiments of the vial and cap holder may include one or more of the clasp frame, the vial holders, the cap holders, and the handle in any combination. While the vial and cap holder is shown in FIG. 1A as including four vial holders and four cap holders, the vial and cap holder can include more or less than four vial holders and four cap holders. For example, the vial and cap holder may include two, three, five, six, seven, eight, nine, ten, or more vial holders, and may include a corresponding number of cap holders.

In one embodiment, clasp frame 100 has a generally round shape (e.g., a ring shape, an ellipsoid shape, or other round shape) where a central portion of the clasp frame is open. The clasp frame may be about 1 inch wide to about 6 inches wide with an inner opening of about 0.75 wide inches to about 5.75 inches wide. The clasp frame may have a height of about 0.125 inches to about 1 inch.

Handle 125 may be integrally formed with the clasp frame or may be attached to the clasp frame by a variety of techniques. For example, the handle may be mechanically attached to the clasp frame via rivets, nuts and bolts, screws, slip fit (e.g., tongue and groove), or other devices. The handle may alternatively be attached to the clasp frame via plastic weld (e.g., epoxy or other glue type substance), thermal weld, or other bonding process. The handle may be about 1 inch long to about 6 inches long, and may be about 0.25 inches wide to about 2 inches wide. The handle may be rounded for comfortable holding in a user's hand.

FIGS. 1B and 1C are a perspective view and a front planar view of the vial and cap holder and show the vial holders attached to an outer surface of the clasp frame according to one embodiment. The vial holders may be integrally formed with the clasp frame or may be attached to the clasp frame by a variety of techniques. For example, the vial holders may be mechanically attached the clasp frame via rivets, nuts and bolts, screws, slip fit (e.g., dovetail type joint), or other devices. The vial holders may alternatively be attached to the clasp frame via plastic weld (e.g., epoxy or other glue type substance), thermal weld, or other bonding process.

The vial holders may be attached to the vial and cap holder at a variety of locations along the clasp frame. For example, the vial holders may be located along an arc of about 180 degrees or less, such as an arc of about 90 degrees or less. The vial and cap holder may be separated by 2 inches or less (e.g., 2 inches, 1.75 inches, 1.5 inches, 1.25 inches, 1.0 inches, 0.75 inches, 0.5 inches, or 0.25 inches), or about 40 degrees or less, such as about 30 degrees or less, 25 degrees or less, 20 degrees or less, 15 degrees or less, or 10 degrees or less.

According to one embodiment, each pair of vial holders and cap holders (e.g., pair 1: vial holder 110a and cap holder 120a; pair 2: vial holder 110b and cap holder 120b; pair 3: vial holder 110c and cap holder 120c, and pair 4: vial holder 110d and cap holder 120d) lie along a common line (e.g., a radius) of vial frame 105. The angular separation between the lines (e.g., radiuses) is about 40 degrees or less, such as about 30 degrees or less.

Figure 2B:
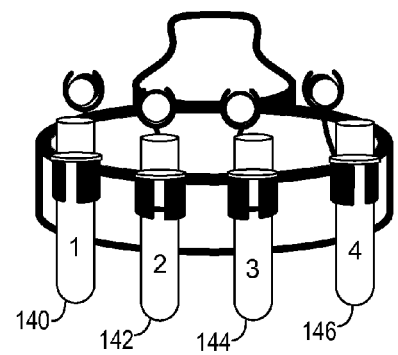
Figure 2C:
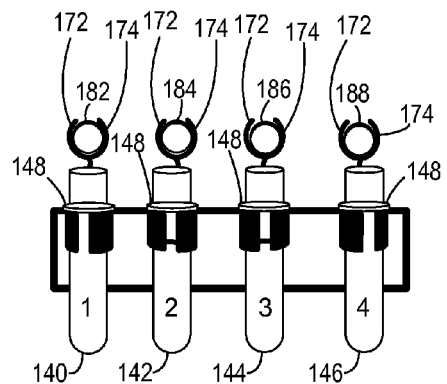

In one embodiment, each vial holder includes a first arm 132 and a second arm 134 where the arms are generally arc shaped and are configured to hold a vial. FIGS. 2A, 2B, and 2C B are a top view, a perspective view, and a front view of the vial and cap holder holding vials 140, 142, 144, and 146 in the vial holders. The vials may be configured for slip on caps, as shown in FIGS. 2A-2C, or may be treaded for receiving threaded caps.

The vial holder may have an inner diameter greater than the outer diameter of the vials or may have an inner diameter less than or equal to the outer diameters of the vials. According to an embodiment where the vial holders have an inner diameter that is greater than the outer diameter of the vials, a vial may be configured to slip into a vial holder and be held in the vial holder by flange 148 on the vial where the flange of the vial contacts the vial holder. Each vial holder has an inner diameter less then a diameter of the flanges so that a flange will contact the vial holder and will not slip down through the vial holder. The inner diameter of the vial holder may be about 0.25 inches or greater, such as about 0.5 inches, 0.75 inches, 1 inch, or greater.

According to an embodiment where the vial holders have an inner diameter that is less than or equal to the outer diameter of the vials, the arms of the vial holders may be configured to flex outward. Specifically, as a vial is pushed into a pair of arms, the arms may flex outward. With the arms in an outward flexed position, the arms exert an inward force on the vial that holds the vial in the arms.

According to one embodiment, each cap holder 120 includes an extension member 150 and a cap clasp 152. Each of the extension members is attached to an inside surface of the vial frame at a first end of the extension member. A second end of the extension member attaches to a corresponding one the cap clasps.

The cap holders 120 may be integrally formed with clasp frame 105 or may be attached to the clasp frame by a variety of techniques. For example, the cap holders may be mechanically attached to the clasp frame via rivets, nuts and bolts, screws, slip fit (e.g., tongue and groove), or other devices. Alternatively, the cap holders may be attached to the clasp frame via plastic weld (e.g., epoxy or other glue type substance), thermal weld, or other bonding process.

In one embodiment, each cap clasp includes a first arm 172 and a second arm 174 where the arms are generally arc shaped and are configured to hold a vial. Each pair of first and second arms meets at a contact location on one of the extensions. FIGS. 2A, 2B, and 2C show the cap clasps holding caps 182, 184, 186, and 188 in arms 172 and 174. While the cap clasps are shown as including first and second arms, the cap clasps may have a variety of alternative shapes for holding the caps. For example, according to an alternative embodiment, the cap clasps may be substantially cylindrical or substantially cylindrical with a side portion opened to allow the cap clasps to bend outward to receive a cap.

Figure 3:
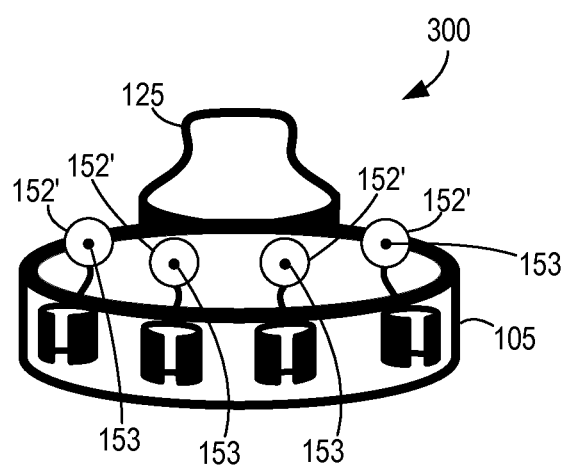
FIG. 3 is a perspective view of the vial and cap holder according to an embodiment where the cap clasps are relatively flat and include one or more adherent devices that respectively adhere the caps to the cap clasps.

FIG. 3 is a perspective view of a vial and cap holder 300 according to an embodiment where the cap clasps 152' are relatively flat and include one or more adherent devices 153 that respectively adhere the caps to the cap clasps. For example, the adherent devices may include an adhesive material where the caps stick to the cap clasps. The adhesive material may be covered by a substantially non-stick material that can be removed from the cap clasp to expose the adhesive material and thereafter the caps may be removably adhered to the adhesive material prior to use of the vial and cap holder. According to another embodiment, the adherent devices includes hook and loop devices, such as Velcro® (a registered trademark of Velcro USA Inc. Manchester N.H.).

According to another embodiment, the adherent devices include a snap device. According to the embodiment, each cap can include a corresponding snap device. The attached snap devices may be configured to allow a cap to rotate while attached to the cap clasp. Providing for the caps to rotate while attached to the cap clasps allows the caps to be threaded onto the vials while attached to the cap clasps. Such attachment provides the benefit, among other things, of allowing a medical practitioner to put a cap fully onto a vial without the chance of a cap being dropped. Snap devices also allow for the caps to be relatively easily unsnapped and unattached from the cap clasps after the caps are threaded onto the vials. The cap clasps and caps can include adherent devices other than snaps that allow the caps to rotate while attached to the cap clasps so that the caps can be threaded onto the veils while attached to cap clasps.

In one embodiment, the vial and cap holders described herein are made at least in part of plastic or other plastic type material, such as nylon, vinyl, acrylic, or other material. The vial and cap holder can also be made of a combination of plastic or plastic type materials. For example, the vial holders and cap clasps may be made of a relatively flexible plastic material, where the clasp frame and handle may be made of relatively rigid plastic material.

Figures 4A, 4B:
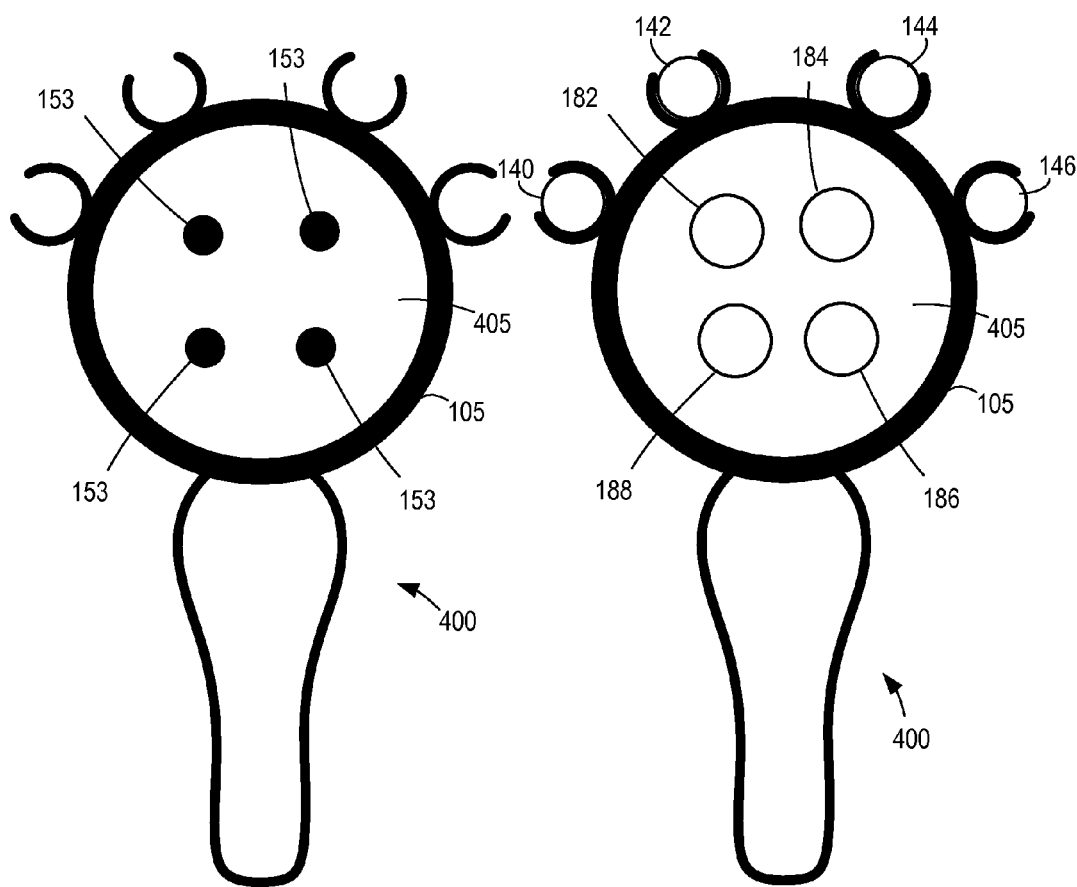
FIGS. 4A and 4B are top views of a vial and cap holder according to another embodiment where the clasp frame includes an inner surface.

FIGS. 4A and 4B are top views of a vial and cap holder 400 according to another embodiment where the clasp frame 105 includes an inner surface 405. The inner surface includes a number of adherent devices 153 positioned on the inner surface where the adherent devices are configured to removably adhere to the caps. FIG. 4B shows a number of caps 182-188 adhered to the adherent devices.

Figure 5:
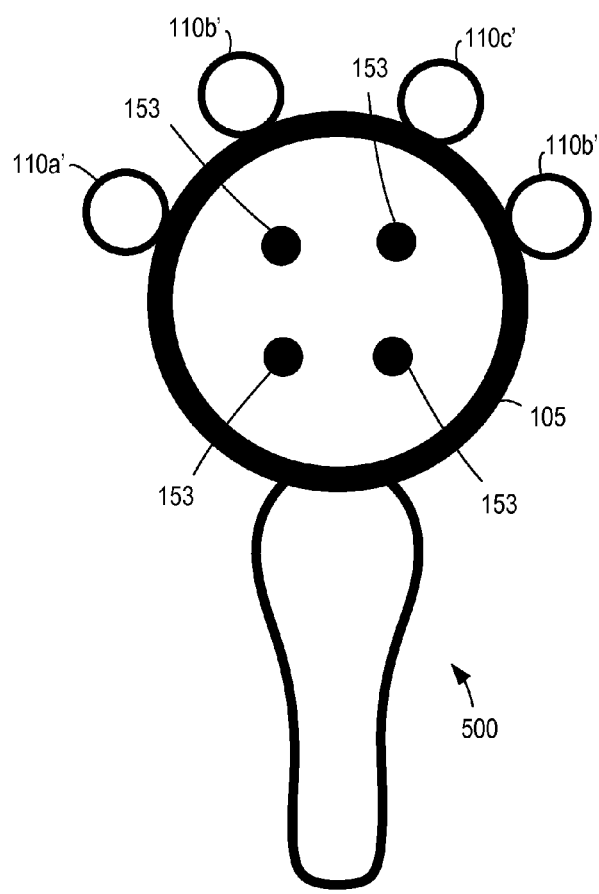
FIG. 5 is a top view of a vial and cap holder according to another embodiment.

FIG. 5 is a top view of a vial and cap holder 500 according to another embodiment. Vial and cap holder 500 includes a number of vial holders 110a', 110b', 110c', and 110d' where the vial holders have a closed shape. The closed shape can be substantially round, such as circular, for holding a set of vials. While vial and cap holder 500 is shown in FIG. 5 as including adherent devices 153 for holding the caps, the vial and cap holder can include cap clasps as shown in FIGS. 1A-1C or otherwise as described herein.

The closed shaped vial holders may have an inner diameter that is larger than the outer diameter of the vials that are configured to be held by the vial holders. Flanges of the vials may be configured to contact the vial holders to hold the vials in the vial holders.

Figure 6:
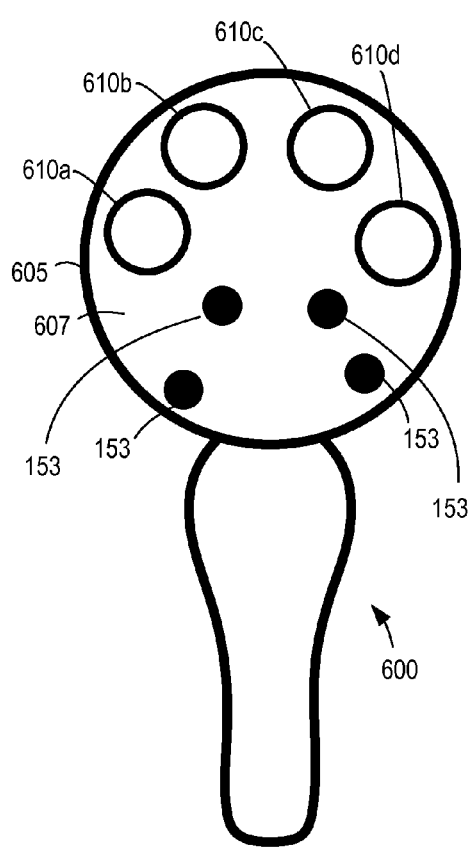
FIG. 6 is a top view of a vial and cap holder according to another embodiment.

FIG. 6 is a top view of a vial and cap holder 600 according to another embodiment. Vial and cap holder 600 includes a vial frame 605 that has an inner surface 607. Inner surface 607 has a number of vial apertures 610a, 610b, 610c, and 610d (generally 610) formed in the inner surface. The vial apertures are configured to receive and hold a set of vials. Each vial aperture has a diameter that is greater than the diameter of the vials and less than the diameter flanges of the vials so that the flanges can contact inner surface 607 with the vials positioned in the apertures. While vial and cap holder 600 is shown as having four vial apertures, the vial and cap holder can have more or fewer vial apertures configured to hold vials.

Apertures 610 can be substantially round, such as circular, for holding a set of vials. While vial and cap holder 600 is shown in FIG. 6 as including adherent devices 153 for holding the caps, the vial and cap holder can include other cap holders, such as the cap holders shown in FIGS. 1A-1C, FIG. 3, or otherwise as described herein. The cap holders can be positioned on a side of the vial frame where the cap holders can be configured to hold the caps adjacent to the tops of the vials while the vials are positioned in the vial apertures.

Figure 7:
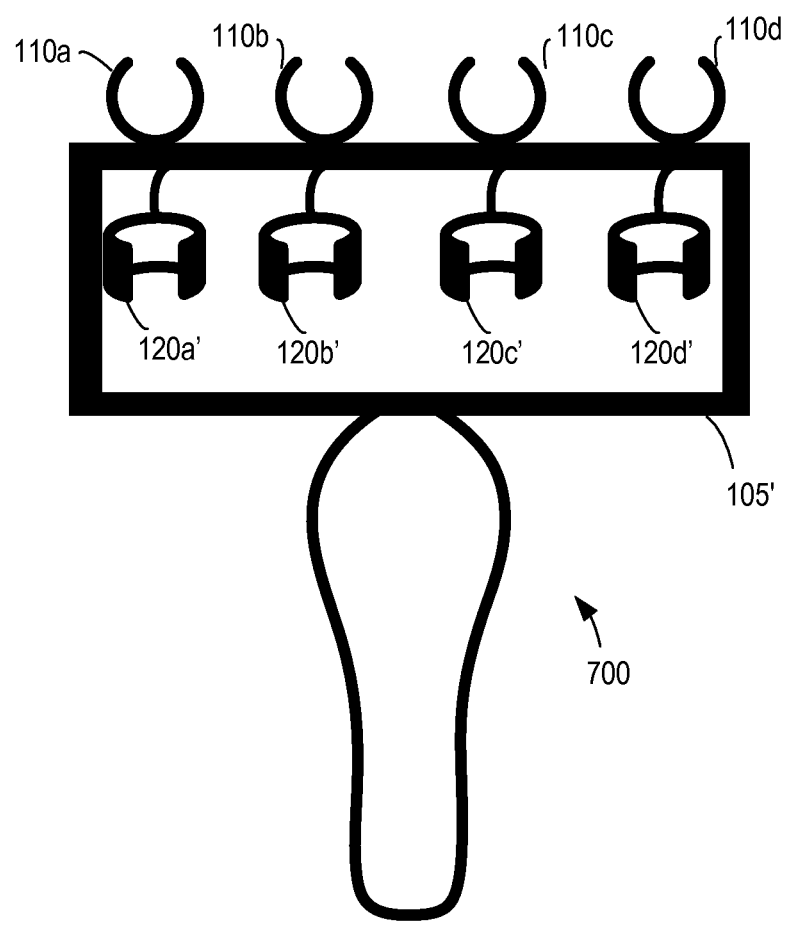
FIG. 7 is a top view of a vial and cap holder according to another embodiment.

FIG. 7 is a top view of a vial and cap holder 700 according to another embodiment. Vial and cap holder 700 is substantially similar to vial and cap holder 100 but vial and cap holder 700 has a clasp frame 105' that is quadrilateral, such as rectangular. While clasp frame 105' is shown as being quadrilateral, the clasp frame can have a variety of other shapes, such as capricious, triangular, pentagonal, or other shapes.

Vial and cap holder 700 also has a number of cap clasps 120a', 120b', 120c', and 120d' that are substantially cylindrical in shape with a side portion that is open to allow the cap clasps to flex outward when caps are placed in the cap clasps. The outward flex provides that an inward force is placed on the caps to hold the caps in place.

According to one alternative embodiment, the caps are attached to the vials, and the embodiments described herein do not include cap holders. The caps can be mounted on the vials for rotating a cap from a side position on a vile to being positioned over the top of the vial for capping the vial.

The vial and cap holders described herein provide a number of benefits for patients and for medical practitioner who take fluid samples and tissue samples from patients. The vial and cap holders provide that a medical practitioner can relatively easily and quickly move the vials into position, for example, at the end of a puncture needle, for taking fluid samples without a patient losing excessive amounts of fluid (e.g., cerebrospinal fluid). For example, during a lumbar puncture, a doctor while holding the vial and cap holder can relatively quickly move the openings of successive vials to the end of the puncture need to capture cerebrospinal fluid to substantially minimize the amount of time that cerebrospinal fluid is collected from the lumbar puncture.

In contrast, during a traditional method of collecting cerebrospinal fluid from a lumbar puncture each vial and cap is handled independently by a doctor. For example, each vial and cap is removed independently from a procedural tray and placed back in the procedural tray after a sample is taken and a vial is capped. More specifically, a first vial may be removed from the procedural tray, the first vial may be moved to the end of the puncture needle where a sample is collected in the first vial, a first cap is then removed from the procedural tray, the vial is capped, and the capped vial is returned to the procedural tray. These steps are repeated for each vial and cap (e.g., often four vials and four caps) while the patients continues to lose cerebrospinal fluid and while the doctor continues to manage the patient, staff, and other pieces of medical equipment in the operating room. Handling each vial and cap independently allows a relatively large amount of cerebrospinal fluid to go un-captured from the puncture needle.

The vial and cap holders described herein allow for relatively minimal loss of uncollected cerebrospinal fluid during a lumbar puncture and thereby provide patients a number of benefits including lowering the patient's likelihood of getting a headache from excessive loose of cerebrospinal fluid or other body aches associated with cerebrospinal fluid loss. The vial and cap holders described herein also allow for a puncture needle to be in place in a patient for a shorter time compared to traditional methods of fluid collection where vials and caps are independently handled over a longer period of time for fluid capture.

The vial and cap holders described herein further provide for a relatively high likelihood of keeping collected sample sterile due the caps for the vials being positioned adjacent to the top openings of the vials on the vial and cap holder. The positioning of a cap adjacent (e.g., 1.5 inches or less, such as 1.25 inches, 1.0 inches, 1.75 inches, 1.5 inches, 1.25 inches, 1.0 inches, 0.75 inches, 0.5 inches, 0.25 inches, 0.2 inches, 0.1 inches) to the top of a corresponding vial provides that each cap can be relatively quickly accessed and thereby the vials can be relatively quickly capped. Quick capping of the vials limits the amount of time that collected sample are exposed to the air of the ambient environment and thereby limits that likelihood that contaminants, such as bacteria, can enter the vials prior to capping. The capped vials can thereafter be removed from the vial and cap holder and sent to a lab for analysis of the samples.

The vial and cap holders described herein also decrease health risks for medical personal who collect patients bodily fluids because individual vials do not need to be held by hand when fluid sample are collected in a vial. Holding the vials at the end of a vial and cap holders while collecting a bodily fluid sample lowers the chance that the bodily fluid will contact a care providers hand or other body parts. Often, samples of bodily fluid are contagious, some highly contagious, and put medical personal at risk of exposure to the samples. For example, in cases were a patient has Creutzfeldt-Jakob disease (CJD), which is a type of mad caw disease, cerebrospinal fluid samples are very contagious, and holding a number of vials with a vial and cap holder described herein can reduce the likelihood that medical personal will contact the vials. According to some embodiments, a procedural tray (described below) is provided in which capped vials can be placed without medical personal contacting the vials while the vials are held by the vial and cap holder and while a care provider holds the handle of the vial and cap holder.

Figure 8:
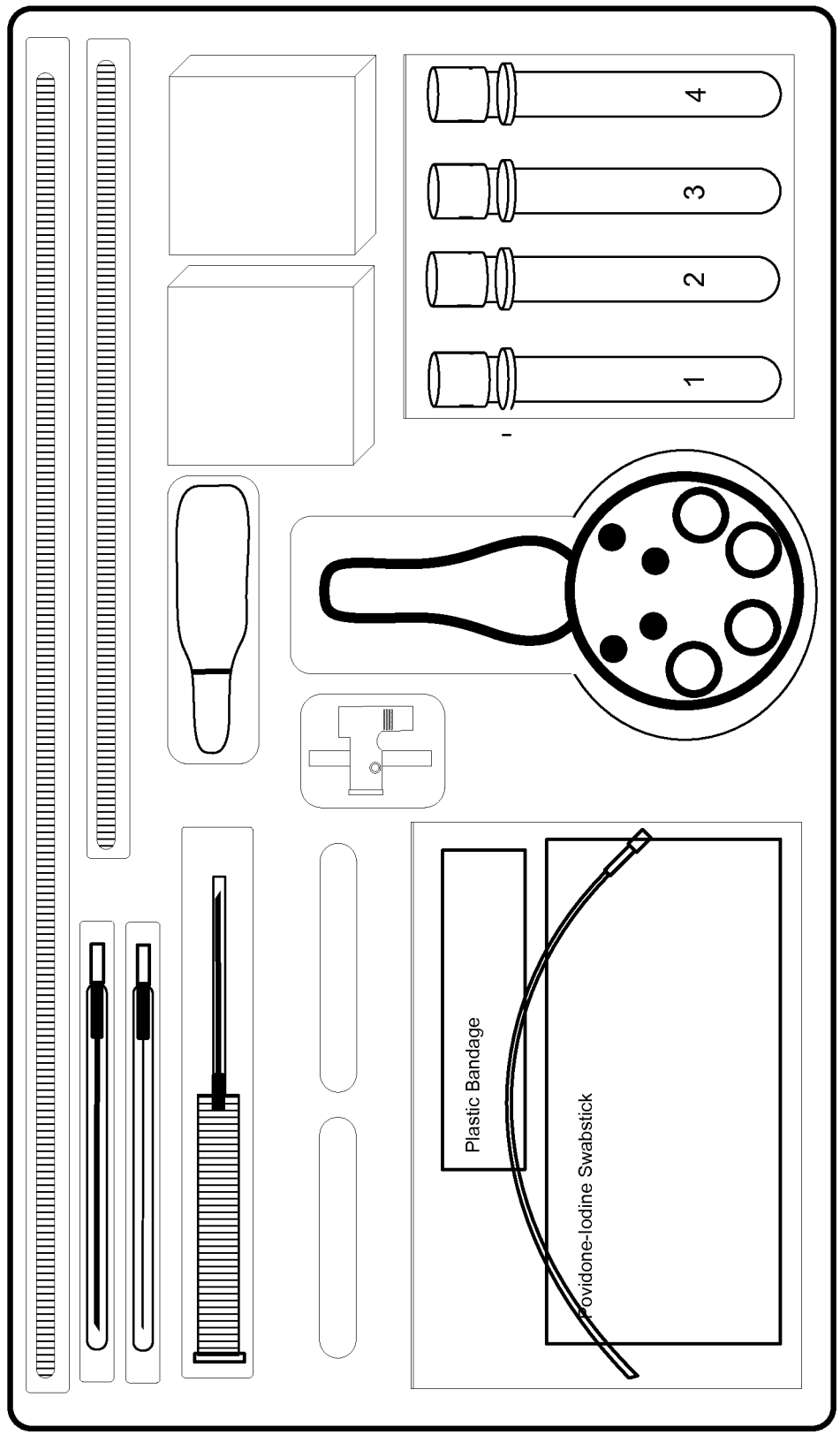
FIG. 8 is a diagram of a procedural tray according to one embodiment.

FIG. 8 is a diagram of a procedural tray according to one embodiment. The procedural tray includes a first portion (e.g., a recessed portion) that is configured to contain the vial and cap holder, and a second portion (e.g., a recessed portion) that is configured to contain the vials and caps. The procedural tray may be a lumbar puncture tray or a tray for a different procedure. While the procedural tray is shown as including a vial and cap holder that is configured to hold four vials and four caps, the vial and cap holder may be configured to hold more or fewer vials and caps. The procedural tray may be plastic and the recessed portions may be in the general shape of the objects being held. The procedural tray may include other items such as various size puncture needles, a syringe, or the like. According to one embodiment, the procedural tray includes a third portion having a number of receptacle portions that are configured to receive the capped vials from the vial and cap holder. The receptacle portions may include recesses, such as four recesses, into which the capped vials held by the vial and cap holder can be placed. The receptacle portions may have a shape (curved or straight) that matches the positions of the vial holders in the vial and cap holder. A user may position the bottom of the vials in the receptacle portions and the vials may thereafter by held by the receptacle portions. The procedural tray may be packaged and then transferred to a lab providing for substantially minimal contact with the vials while sample are collected.

This description of the invention has been presented for the purposes of illustration and description. It is not intended to be exhaustive or to limit the invention to the precise form described, and many modifications and variations are possible in light of the teaching above. The implementations were chosen and described in order to best explain the principles of the invention and its practical applications. This description will enable others skilled in the art to best utilize and practice the invention in various implementations and with various modifications as are suited to a particular use. The scope of the invention is defined by the following claims.

The invention claimed is:

1. A vial and cap holder comprising:
a vial frame;
a handle connected to the vial frame;
a plurality of vial holders connected to an outer surface of the vial frame, wherein each vial holder is configured to receive and hold a vial;
a plurality of cap holders connected to an inner surface of the vial frame, wherein each of the cap holders is positioned opposite to a corresponding one of the vial holders on the vial frame, and each cap holder is configured to hold a cap for capping a vial.

2. The vial and cap holder of claim 1, wherein the vial frame is a loop.

3. The vial and cap holder of claim 1, wherein the vial frame is a quadrilateral loop.

4. The vial and cap holder of claim 1, wherein at least a portion of each of the vial holders includes a substantially tube-shaped element.

5. The vial and cap holder of claim 4, wherein each of the substantially tube-shaped elements is substantially cylindrical.

6. The vial and cap holder of claim 4, wherein each of the substantially tube-shaped elements has an opening formed in a side of the substantially tube-shaped element and the substantially tube-shaped element is configured to flex away from the opening and towards the opening.

7. The vial and cap holder of claim 6, wherein in a position where each of the substantially tube-shaped elements is flexed away from the opening in the substantially tube-shaped element, the substantially tube-shaped element is configured to exert and inward force on a vial positioned in the substantially tube-shaped element.

8. The vial and cap holder of claim 6, wherein each of the openings extends from a first end of one of the substantially tube-shaped elements to a second end of the one of the substantially tube-shaped elements.

9. The vial and cap holder of claim 1, wherein each of the cap holders comprises:
   an extension member; and
   a cap clasp, wherein each of the extension members connects to the vial frame and connects to one of the cap clasps.

10. The vial and cap holder of claim 9, wherein each of the cap clasps comprises a closed ring.

11. The vial and cap holder of claim 10, wherein each of the cap clasps comprises a first arm and a second arm that are configured to flex to hold a cap for a vial.

12. The vial and cap holder of claim 1, wherein adjacent ones of the vial holders are positioned at thirty degrees or less apart along the vial frame with respect to a center of the vial frame.

13. The vial and cap holder of claim 1, wherein corresponding ones of the vial holders and the cap holders are positioned along common radiuses of the vial frame.

14. A vial and cap holder comprising:
   a vial frame having a plurality of vial apertures formed therein, wherein each vial aperture is configured to receive a vial;
   a handle connected to the vial frame; and
   a plurality of cap holders connected to the vial frame, wherein:
   each of the cap holders is positioned adjacent to one of the apertures on the vial frame,
   each cap holder is configured to hold a cap for capping a vial,
   each of the cap holders is configured to hold a cap above a top of a vial that is held by one of the vial apertures, and
   corresponding ones of the vial holders and the cap holders are positioned along common radiuses of the vial frame.

15. The vial and cap holder of claim 14, wherein each of the cap holders is configured to allow a cap held by the cap holder to rotate with respect to the cap holder for threading the cap onto a vial.

16. The vial and cap holder of claim 14, wherein each of the cap holders comprises:
   an extension member; and
   a cap clasp, wherein each of the extension members connects to the vial frame and connects to one of the cap clasps.

17. The vial and cap holder of claim 16, wherein the cap clasp is a closed ring.

18. The vial and cap holder of claim 16, wherein the cap clasp includes a first arm and a second arm that are configured to flex to hold a cap for a vial.

19. A vial and cap holder comprising:
   a vial frame;
   a handle connected to the vial frame;
   a plurality of vial holders connected to an outer surface of the vial frame, wherein each vial holder is configured to receive and hold a vial;
   a plurality of cap holders connected to an inner surface of the vial frame, wherein:
   each of the cap holders is positioned opposite to a corresponding one of the vial holders on the vial frame, and each cap holder is configured to hold a cap for capping a vial,
   at least a portion of each of the vial holders and each of the cap holders comprises a substantially tube-shaped element having an opening formed in a side of the substantially tube-shaped element and the substantially tube-shaped element is configured to flex away from the opening and towards the opening for holding a vial and cap, respectively,
   each of the cap holders is configured to hold a cap above a top of a vial that is held by one of the vial apertures, and
   corresponding ones of the vial holders and the cap holders are positioned along common radiuses of the vial frame.

20. The vial and cap holder of claim 19, wherein adjacent ones of the vial holders are positioned at thirty degrees or less apart along the vial frame with respect to a center of the vial frame.

\* \* \* \* \*